(12) United States Patent
Schweighoffer et al.

(10) Patent No.: US 6,544,948 B1
(45) Date of Patent: *Apr. 8, 2003

(54) ΔP62, VARIANTS THEREOF, AMINO ACID SEQUENCES CODING THEREFOR AND THEIR USES IN GENE THERAPY FOR CANCER

(75) Inventors: Fabien Schweighoffer, Vincennes (FR); Bruno Tocque, Courbevoie (FR)

(73) Assignee: Aventis Pharma S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,899
(22) PCT Filed: May 29, 1996
(86) PCT No.: PCT/FR96/00802
  § 371 (c)(1),
  (2), (4) Date: Nov. 25, 1997
(87) PCT Pub. No.: WO96/38556
  PCT Pub. Date: Dec. 5, 1996

(30) Foreign Application Priority Data

Jun. 1, 1995 (FR) .............................. 95 06533

(51) Int. Cl.[7] .......................... A61K 38/16; C07K 14/00
(52) U.S. Cl. ........................ 514/12; 530/350; 536/23.1; 536/23.5
(58) Field of Search ..................... 530/350; 536/23.1, 536/23.5; 435/320.1; 514/12

(56) References Cited

FOREIGN PATENT DOCUMENTS

WO    WO 92/20794    11/1992

OTHER PUBLICATIONS

Miller, A. et al., Mol. Cell. Biol., vol. 5, No. 3, pp. 431–437, Mar. 1985.*

Mitani, K. et al., Proc. Natl. Acad. Sci. USA, vol. 92, pp. 3854–3858, Apr. 1995.*

Amann, E. et al., Gene, vol. 69, pp. 301–315, 1988.*

Wang et al., p62 Association with RNA is Regulated by Tyrosine Phosphorylation*, The Journal of Biological Chemistry 270(5), 2010–2013 (1995).

Richard et al., Association of p62, Multifunctional SH2– and SH3–Domain–Binding Protein, with src Family Tyrosine Kinases, Grb2, and Phospholipase Cγ–1, Molecular & Cellular Biology, 15(1) 186–197 (1995).

Siomi et al., Essential Role for KH Domains in RNA Binding: Impaired RNA Binding by a Mutation in the KH Domain of FMR1 That Causes Fragile X Syndrome, Cell 77 33–39 (1994).

Wisniewski et al., A 62–Kilodalton Tyrosine Phosphoprotein Constitutively Present in Primary Chronic Phase Chronic Myelogenous Leukemia Enriched Lineage Negative Blast Populations, Leukemia 8(4) 688–693 (1994).

Wong et al., Molecular Cloning and Nucleic Acid Binding Properties of the GAP–Associated Tyrosine Phosphoprotein p62, Cell 69 551–558 (1992).

* cited by examiner

*Primary Examiner*—Nashaat T. Nashed
(74) *Attorney, Agent, or Firm*—Finnegan, Henderson, Farabow, Garrett & Dunner LLP

(57) ABSTRACT

A polypeptide derivative of p62 having at least one deletion of at least one amino acid between amino acids 145 to 247 of p62, where the derivative inhibits signals transduced by ras.

6 Claims, 5 Drawing Sheets

NIH3T3

+ΔP62

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1332 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1332

(xi) SEQUENCE DESCRIPTION: SEQ ID NO:1:

```
ATG CAG CGC CGG GAC GAC CCC GCC GCG CGC ATG AGC CGG TCT TCG GGC      48
Met Gln Arg Arg Asp Asp Pro Ala Ala Arg Met Ser Arg Ser Ser Gly
 1               5                  10                  15

CGT AGC GGC TCC ATG GAC CCC TCC GGT GCC CAC CCC TCG GTG CGT CAG      96
Arg Ser Gly Ser Met Asp Pro Ser Gly Ala His Pro Ser Val Arg Gln
             20                  25                  30

ACG CCG TCT CGG CAG CCG CCG CTG CCT CAC CGG TCC CGG GGA GGC GGA     144
Thr Pro Ser Arg Gln Pro Pro Leu Pro His Arg Ser Arg Gly Gly Gly
         35                  40                  45

GGG GGA TCC CGC GGG GGC GCC CGG GCC TCG CCC GCC ACG CAG CCG CCA     192
Gly Gly Ser Arg Gly Gly Ala Arg Ala Ser Pro Ala Thr Gln Pro Pro
 50                  55                  60

CCG CTG CTG CCG CCC TCG GCC ACG GGT CCC GAC GCG ACA GTG GGC GGG     240
Pro Leu Leu Pro Pro Ser Ala Thr Gly Pro Asp Ala Thr Val Gly Gly
 65                  70                  75                  80

CCA GCG CCG ACC CCG CTG CTG CCC CCC TCG GCC ACA GCC TCG GTC AAG     288
Pro Ala Pro Thr Pro Leu Leu Pro Pro Ser Ala Thr Ala Ser Val Lys
             85                  90                  95

ATG GAG CCA GAG AAC AAG TAC CTG CCC GAA CTC ATG GCC GAG AAG GAC     336
Met Glu Pro Glu Asn Lys Tyr Leu Pro Glu Leu Met Ala Glu Lys Asp
            100                 105                 110

TCG CTC GAC CCG TCC TTC ACT CAC GCC ATG CAG CTG CTG ACG GCA GAA     384
Ser Leu Asp Pro Ser Phe Thr His Ala Met Gln Leu Leu Thr Ala Glu
        115                 120                 125

ATT GAG AAG ATT CAG AAA GGA GAC TCA AAA AAG GAT GAT GAG GAG AAT     432
Ile Glu Lys Ile Gln Lys Gly Asp Ser Lys Lys Asp Asp Glu Glu Asn
    130                 135                 140

TAC TTG GAT TTA TTT TCT CAT AAG AAC ATG AAA CTG AAA GAG CGA GTG     480
Tyr Leu Asp Leu Phe Ser His Lys Asn Met Lys Leu Lys Glu Arg Val
145                 150                 155                 160

CTG ATA CCT GTC AAG CAG TAT CCC AAG TTC AAT TTT GTG GGG AAG ATT     528
Leu Ile Pro Val Lys Gln Tyr Pro Lys Phe Asn Phe Val Gly Lys Ile
                165                 170                 175
```

```
CTT GGA CCA CAA GGG AAT ACA ATC AAA AGA CTG CAG GAA GAG ACT GGT        576
Leu Gly Pro Gln Gly Asn Thr Ile Lys Arg Leu Gln Glu Glu Thr Gly
            180                 185                 190

GCA AAG ATC TCT GTA TTG GGA AAG GGC TCA ATG AGA GAC AAA GCC AAG        624
Ala Lys Ile Ser Val Leu Gly Lys Gly Ser Met Arg Asp Lys Ala Lys
            195                 200                 205

GAG GAA GAG CTG CGC AAA GGT GGA GAC CCC AAA TAT GCC CAC TTG AAT        672
Glu Glu Glu Leu Arg Lys Gly Gly Asp Pro Lys Tyr Ala His Leu Asn
    210                 215                 220

ATG GAT CTG CAT GTC TTC ATT GAA GTC TTT GGA CCC CCA TGT GAG GCT        720
Met Asp Leu His Val Phe Ile Glu Val Phe Gly Pro Pro Cys Glu Ala
225                 230                 235                 240

TAT GCT CTT ATG GCC CAT GCC ATG GAG GAA GTC AAG AAA TTT CTA GTA        768
Tyr Ala Leu Met Ala His Ala Met Glu Glu Val Lys Lys Phe Leu Val
                245                 250                 255

CCG GAT ATG ATG GAT GAT ATC TGT CAG GAG CAA TTT CTA GAG CTG TCC        816
Pro Asp Met Met Asp Asp Ile Cys Gln Glu Gln Phe Leu Glu Leu Ser
            260                 265                 270

TAC TTG AAT GGA GTA CCT GAA CCC TCT CGT GGA CGT GGG GTG CCA GTG        864
Tyr Leu Asn Gly Val Pro Glu Pro Ser Arg Gly Arg Gly Val Pro Val
            275                 280                 285

AGA GGC CGG GGA GCT GCA CCT CCT CCA CCA CCT GTT CCC AGG GGC CGT        912
Arg Gly Arg Gly Ala Ala Pro Pro Pro Pro Pro Val Pro Arg Gly Arg
290                 295                 300

GGT GTT GGA CCA CCT CGG GGG GCT TTG GTA CGT GGT ACA CCA GTA AGG        960
Gly Val Gly Pro Pro Arg Gly Ala Leu Val Arg Gly Thr Pro Val Arg
305                 310                 315                 320

GGA GCC ATC ACC AGA GGT GCC ACT GTG ACT CGA GGC GTG CCA CCC CCA       1008
Gly Ala Ile Thr Arg Gly Ala Thr Val Thr Arg Gly Val Pro Pro Pro
                325                 330                 335

CCT ACT GTG AGG GGT GCT CCA GCA CCA AGA GCA CGG ACA GCG GGC ATC       1056
Pro Thr Val Arg Gly Ala Pro Ala Pro Arg Ala Arg Thr Ala Gly Ile
            340                 345                 350

CAG AGG ATA CCT TTG CCT CCA CCT CCT GCA CCA GAA ACA TAT GAA GAA       1104
Gln Arg Ile Pro Leu Pro Pro Pro Pro Ala Pro Glu Thr Tyr Glu Glu
            355                 360                 365

TAT GGA TAT GAT GAT ACA TAC GCA GAA CAA AGT TAC GAA GGC TAC GAA       1152
Tyr Gly Tyr Asp Asp Thr Tyr Ala Glu Gln Ser Tyr Glu Gly Tyr Glu
            370                 375                 380

GGC TAT TAC AGC CAG AGT CAA GGG GAC TCA GAA TAT TAT GAC TAT GGA       1200
Gly Tyr Tyr Ser Gln Ser Gln Gly Asp Ser Glu Tyr Tyr Asp Tyr Gly
385                 390                 395                 400

CAT GGG GAG GTT CAA GAT TCT TAT GAA GCT TAT GGC CAG GAC GAC TGG       1248
His Gly Glu Val Gln Asp Ser Tyr Glu Ala Tyr Gly Gln Asp Asp Trp
                405                 410                 415

AAT GGG ACC AGG CCG TCG CTG AAG GCC CCT CCT GCT AGG CCA GTG AAG       1296
Asn Gly Thr Arg Pro Ser Leu Lys Ala Pro Pro Ala Arg Pro Val Lys
            420                 425                 430

GGA GCA TAC AGA GAG CAC CCA TAT GGA CGT TAT TAA                       1332
Gly Ala Tyr Arg Glu His Pro Tyr Gly Arg Tyr *
            435                 440
```

(2) INFORMATION FOR SEQ ID NO:2:

(i) SEQUENCE CHARACTERISTICS:
        (A) LENGTH: 443 amino acids
        (B) TYPE: amino acid
        (D) TOPOLOGY: linear (ii) MOLECULE TYPE: protein (xi) SEQUENCE DESCRIPTION: SEQ ID NO:2:

-continued

```
Met Gln Arg Arg Asp Asp Pro Ala Ala Arg Met Ser Arg Ser Ser Gly
 1               5                  10                 15

Arg Ser Gly Ser Met Asp Pro Ser Gly Ala His Pro Ser Val Arg Gln
            20                  25                 30

Thr Pro Ser Arg Gln Pro Pro Leu Pro His Arg Ser Arg Gly Gly Gly
        35                  40                 45

Gly Gly Ser Arg Gly Gly Ala Arg Ala Ser Pro Ala Thr Gln Pro Pro
    50                  55                 60

Pro Leu Leu Pro Pro Ser Ala Thr Gly Pro Asp Ala Thr Val Gly Gly
65                  70                  75                 80

Pro Ala Pro Thr Pro Leu Leu Pro Pro Ser Ala Thr Ala Ser Val Lys
                85                  90                 95

Met Glu Pro Glu Asn Lys Tyr Leu Pro Glu Leu Met Ala Glu Lys Asp
            100                 105                110

Ser Leu Asp Pro Ser Phe Thr His Ala Met Gln Leu Leu Thr Ala Glu
            115                 120                125

Ile Glu Lys Ile Gln Lys Gly Asp Ser Lys Lys Asp Asp Gly Glu Asn
        130                 135             140

Tyr Leu Asp Leu Phe Ser His Lys Asn Met Lys Leu Lys Glu Arg Val
145                 150                 155                160

Leu Ile Pro Val Lys Gln Tyr Pro Lys Phe Asn Phe Val Gly Lys Ile
                165                 170             175

Leu Gly Pro Gln Gly Asn Thr Ile Lys Arg Leu Gln Glu Glu Thr Gly
            180                 185                 190

Ala Lys Ile Ser Val Leu Gly Lys Gly Ser Met Arg Asp Lys Ala Lys
        195                 200                 205

Glu Glu Glu Leu Arg Lys Gly Gly Asp Pro Lys Tyr Ala His Leu Asn
    210                 215                 220

Met Asp Leu His Val Phe Ile Glu Val Phe Gly Pro Pro Cys Glu Ala
225                 230                 235                240

Tyr Ala Leu Met Ala His Ala Met Glu Glu Val Lys Lys Phe Leu Val
                245                 250                 255

Pro Asp Met Met Asp Asp Ile Cys Gln Glu Gln Phe Leu Glu Leu Ser
            260                 265                 270

Tyr Leu Asn Gly Val Pro Glu Pro Ser Arg Gly Arg Gly Val Pro Val
        275                 280                 285

Arg Gly Arg Gly Ala Ala Pro Pro Pro Val Pro Arg Gly Arg
    290                 295                 300

Gly Val Gly Pro Pro Arg Gly Ala Leu Val Arg Gly Thr Pro Val Arg
305                 310                 315                320

Gly Ala Ile Thr Arg Gly Ala Thr Val Thr Arg Gly Val Pro Pro Pro
                325                 330                 335

Pro Thr Val Arg Gly Ala Pro Ala Pro Arg Ala Arg Thr Ala Gly Ile
            340                 345                 350

Gln Arg Ile Pro Leu Pro Pro Pro Ala Pro Glu Thr Tyr Glu Glu
        355                 360                 365

Tyr Gly Tyr Asp Asp Thr Tyr Ala Glu Gln Ser Tyr Glu Gly Tyr Glu
    370                 375                 380

Gly Tyr Tyr Ser Gln Ser Gln Gly Asp Ser Glu Tyr Tyr Asp Tyr Gly
385                 390                 395                400

His Gly Glu Val Gln Asp Ser Tyr Glu Ala Tyr Gly Gln Asp Asp Trp
                405                 410                 415
```

-continued

```
Asn Gly Thr Arg Pro Ser Leu Lys Ala Pro Pro Ala Arg Pro Val Lys
            420                 425                 430
Gly Ala Tyr Arg Glu His Pro Tyr Gly Arg Tyr
            435                 440

(2) INFORMATION FOR SEQ ID NO:3:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1215

(xi) SEQUENCE DESCRIPTION: SEQ ID NO:3:

ATG CAG CGC CGG GAC GAC CCC GCC GCG CGC ATG AGC CGG TCT TCG GGC         48
Met Gln Arg Arg Asp Asp Pro Ala Ala Arg Met Ser Arg Ser Ser Gly
445                 450                 455                 460

CGT AGC GGC TCC ATG GAC CCC TCC GGT GCC CAC CCC TCG GTG CGT CAG         96
Arg Ser Gly Ser Met Asp Pro Ser Gly Ala His Pro Ser Val Arg Gln
                465                 470                 475

ACG CCG TCT CGG CAG CCG CCG CTG CCT CAC CGG TCC CGG GGA GGC GGA        144
Thr Pro Ser Arg Gln Pro Pro Leu Pro His Arg Ser Arg Gly Gly Gly
            480                 485                 490

GGG GGA TCC CGC GGG GGC GCC CGG GCC TCG CCC GCC ACG CAG CCG CCA        192
Gly Gly Ser Arg Gly Gly Ala Arg Ala Ser Pro Ala Thr Gln Pro Pro
            495                 500                 505

CCG CTG CTG CCG CCC TCG GCC ACG GGT CCC GAC GCG ACA GTG GGC GGG        240
Pro Leu Leu Pro Pro Ser Ala Thr Gly Pro Asp Ala Thr Val Gly Gly
    510                 515                 520

CCA GCG CCG ACC CCG CTG CTG CCC CCC TCG GCC ACA GCC TCG GTC AAG        288
Pro Ala Pro Thr Pro Leu Leu Pro Pro Ser Ala Thr Ala Ser Val Lys
525                 530                 535                 540

ATG GAG CCA GAG AAC AAG TAC CTG CCC GAA CTC ATG GCC GAG AAG GAC        336
Met Glu Pro Glu Asn Lys Tyr Leu Pro Glu Leu Met Ala Glu Lys Asp
                545                 550                 555

TCG CTC GAC CCG TCC TTC ACT CAC GCC ATG CAG CTG CTG ACG GCA GAA        384
Ser Leu Asp Pro Ser Phe Thr His Ala Met Gln Leu Leu Thr Ala Glu
            560                 565                 570

ATT GAG AAG ATT CAG AAA GGA GAC TCA AAA AAG GAT GAT GAG GAG AAT        432
Ile Glu Lys Ile Gln Lys Gly Asp Ser Lys Lys Asp Asp Glu Glu Asn
            575                 580                 585

TAC TTG GAT TTA TTT TCT CAT AAG AAC ATG AAA CTG AAA GAG CGA GTG        480
Tyr Leu Asp Leu Phe Ser His Lys Asn Met Lys Leu Lys Glu Arg Val
    590                 595                 600

CTG ATA CCT GTC AAG CAG TAT CCC AAG GAG GAA GAG CTG CGC AAA GGT        528
Leu Ile Pro Val Lys Gln Tyr Pro Lys Glu Glu Glu Leu Arg Lys Gly
605                 610                 615                 620

GGA GAC CCC AAA TAT GCC CAC TTG AAT ATG GAT CTG CAT GTC TTC ATT        576
Gly Asp Pro Lys Tyr Ala His Leu Asn Met Asp Leu His Val Phe Ile
                625                 630                 635

GAA GTC TTT GGA CCC CCA TGT GAG GCT TAT GCT CTT ATG GCC CAT GCC        624
Glu Val Phe Gly Pro Pro Cys Glu Ala Tyr Ala Leu Met Ala His Ala
            640                 645                 650

ATG GAG GAA GTC AAG AAA TTT CTA GTA CCG GAT ATG ATG GAT GAT ATC        672
Met Glu Glu Val Lys Lys Phe Leu Val Pro Asp Met Met Asp Asp Ile
            655                 660                 665
```

-continued

```
TGT CAG GAG CAA TTT CTA GAG CTG TCC TAC TTG AAT GGA GTA CCT GAA     720
Cys Gln Glu Gln Phe Leu Glu Leu Ser Tyr Leu Asn Gly Val Pro Glu
    670                 675                 680

CCC TCT CGT GGA CGT GGG GTG CCA GTG AGA GGC CGG GGA GCT GCA CCT     768
Pro Ser Arg Gly Arg Gly Val Pro Val Arg Gly Arg Gly Ala Ala Pro
685                 690                 695                 700

CCT CCA CCA CCT GTT CCC AGG GGC CGT GGT GTT GGA CCA CCT CGG GGG     816
Pro Pro Pro Pro Val Pro Arg Gly Arg Gly Val Gly Pro Pro Arg Gly
                705                 710                 715

GCT TTG GTA CGT GGT ACA CCA GTA AGG GGA GCC ATC ACC AGA GGT GCC     864
Ala Leu Val Arg Gly Thr Pro Val Arg Gly Ala Ile Thr Arg Gly Ala
            720                 725                 730

ACT GTG ACT CGA GGC GTG CCA CCC CCA CCT ACT GTG AGG GGT GCT CCA     912
Thr Val Thr Arg Gly Val Pro Pro Pro Pro Thr Val Arg Gly Ala Pro
        735                 740                 745

GCA CCA AGA GCA CGG ACA GCG GGC ATC CAG AGG ATA CCT TTG CCT CCA     960
Ala Pro Arg Ala Arg Thr Ala Gly Ile Gln Arg Ile Pro Leu Pro Pro
    750                 755                 760

CCT CCT GCA CCA GAA ACA TAT GAA GAA TAT GGA TAT GAT GAT ACA TAC    1008
Pro Pro Ala Pro Glu Thr Tyr Glu Glu Tyr Gly Tyr Asp Asp Thr Tyr
765                 770                 775                 780

GCA GAA CAA AGT TAC GAA GGC TAC GAA GGC TAT TAC AGC CAG AGT CAA    1056
Ala Glu Gln Ser Tyr Glu Gly Tyr Glu Gly Tyr Tyr Ser Gln Ser Gln
                785                 790                 795

GGG GAC TCA GAA TAT TAT GAC TAT GGA CAT GGG GAG GTT CAA GAT TCT    1104
Gly Asp Ser Glu Tyr Tyr Asp Tyr Gly His Gly Glu Val Gln Asp Ser
            800                 805                 810

TAT GAA GCT TAT GGC CAG GAC GAC TGG AAT GGG ACC AGG CCG TCG CTG    1152
Tyr Glu Ala Tyr Gly Gln Asp Asp Trp Asn Gly Thr Arg Pro Ser Leu
        815                 820                 825

AAG GCC CCT CCT GCT AGG CCA GTG AAG GGA GCA TAC AGA GAG CAC CCA    1200
Lys Ala Pro Pro Ala Arg Pro Val Lys Gly Ala Tyr Arg Glu His Pro
    830                 835                 840

TAT GGA CGT TAT TAA                                                1215
Tyr Gly Arg Tyr *
845
```

(2) INFORMATION FOR SEQ ID NO:4:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gln Arg Arg Asp Asp Pro Ala Ala Arg Met Ser Arg Ser Ser Gly
1               5                  10                  15

Arg Ser Gly Ser Met Asp Pro Ser Gly Ala His Pro Ser Val Arg Gln
            20                  25                  30

Thr Pro Ser Arg Gln Pro Pro Leu Pro His Arg Ser Arg Gly Gly Gly
        35                  40                  45

Gly Gly Ser Arg Gly Gly Ala Arg Ala Ser Pro Ala Thr Gln Pro Pro
    50                  55                  60

Pro Leu Leu Pro Pro Ser Ala Thr Gly Pro Asp Ala Thr Val Gly Gly
65                  70                  75                  80

Pro Ala Pro Thr Pro Leu Leu Pro Pro Ser Ala Thr Ala Ser Val Lys
                85                  90                  95

Met Glu Pro Glu Asn Lys Tyr Leu Pro Glu Leu Met Ala Glu Lys Asp
```

-continued

```
                100                 105                 110
    Ser Leu Asp Pro Ser Phe Thr His Ala Met Gln Leu Leu Thr Ala Glu
                115                 120                 125

Ile Glu Lys Ile Gln Lys Gly Asp Ser Lys Lys Asp Asp Glu Glu Asn
            130                 135                 140

Tyr Leu Asp Leu Phe Ser His Lys Asn Met Lys Leu Lys Glu Arg Val
    145                 150                 155                 160

Leu Ile Pro Val Lys Gln Tyr Pro Lys Glu Glu Leu Arg Lys Gly
                    165                 170                 175

Gly Asp Pro Lys Tyr Ala His Leu Asn Met Asp Leu His Val Phe Ile
                180                 185                 190

Glu Val Phe Gly Pro Pro Cys Glu Ala Tyr Ala Leu Met Ala His Ala
                195                 200                 205

Met Glu Glu Val Lys Lys Phe Leu Val Pro Asp Met Met Asp Asp Ile
            210                 215                 220

Cys Gln Glu Gln Phe Leu Glu Leu Ser Tyr Leu Asn Gly Val Pro Glu
    225                 230                 235                 240

Pro Ser Arg Gly Arg Gly Val Pro Val Arg Gly Arg Gly Ala Ala Pro
                    245                 250                 255

Pro Pro Pro Pro Val Pro Arg Gly Arg Gly Val Gly Pro Pro Arg Gly
                260                 265                 270

Ala Leu Val Arg Gly Thr Pro Val Arg Gly Ala Ile Thr Arg Gly Ala
                275                 280                 285

Thr Val Thr Arg Gly Val Pro Pro Pro Thr Val Arg Gly Ala Pro
            290                 295                 300

Ala Pro Arg Ala Arg Thr Ala Gly Ile Gln Arg Ile Pro Leu Pro Pro
    305                 310                 315                 320

Pro Pro Ala Pro Glu Thr Tyr Glu Glu Tyr Gly Tyr Asp Asp Thr Tyr
                    325                 330                 335

Ala Glu Gln Ser Tyr Glu Gly Tyr Glu Gly Tyr Tyr Ser Gln Ser Gln
                340                 345                 350

Gly Asp Ser Glu Tyr Tyr Asp Tyr Gly His Gly Glu Val Gln Asp Ser
                355                 360                 365

Tyr Glu Ala Tyr Gly Gln Asp Asp Trp Asn Gly Thr Arg Pro Ser Leu
    370                 375                 380

Lys Ala Pro Pro Ala Arg Pro Val Lys Gly Ala Tyr Arg Glu His Pro
    385                 390                 395                 400

Tyr Gly Arg Tyr
```

(2) INFORMATION FOR SEQ ID NO:5:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..726

(xi) SEQUENCE DESCRIPTION: SEQ ID NO:5:

```
ATG AGA GAC AAA GCC AAG GAG GAA GAG CTG CGC AAA GGT GGA GAC CCC    48
Met Arg Asp Lys Ala Lys Glu Glu Glu Leu Arg Lys Gly Gly Asp Pro
            410                 415                 420
```

```
AAA TAT GCC CAC TTG AAT ATG GAT CTG CAT GTC TTC ATT GAA GTC TTT     96
Lys Tyr Ala His Leu Asn Met Asp Leu His Val Phe Ile Glu Val Phe
            425                 430                 435

GGA CCC CCA TGT GAG GCT TAT GCT CTT ATG GCC CAT GCC ATG GAG GAA    144
Gly Pro Pro Cys Glu Ala Tyr Ala Leu Met Ala His Ala Met Glu Glu
            440                 445                 450

GTC AAG AAA TTT CTA GTA CCG GAT ATG ATG GAT GAT ATC TGT CAG GAG    192
Val Lys Lys Phe Leu Val Pro Asp Met Met Asp Asp Ile Cys Gln Glu
    455                 460                 465

CAA TTT CTA GAG CTG TCC TAC TTG AAT GGA GTA CCT GAA CCC TCT CGT    240
Gln Phe Leu Glu Leu Ser Tyr Leu Asn Gly Val Pro Glu Pro Ser Arg
470                 475                 480                 485

GGA CGT GGG GTG CCA GTG AGA GGC CGG GGA GCT GCA CCT CCT CCA CCA    288
Gly Arg Gly Val Pro Val Arg Gly Arg Gly Ala Ala Pro Pro Pro Pro
                490                 495                 500

CCT GTT CCC AGG GGC CGT GGT GTT GGA CCA CCT CGG GGG GCT TTG GTA    336
Pro Val Pro Arg Gly Arg Gly Val Gly Pro Pro Arg Gly Ala Leu Val
            505                 510                 515

CGT GGT ACA CCA GTA AGG GGA GCC ATC ACC AGA GGT GCC ACT GTG ACT    384
Arg Gly Thr Pro Val Arg Gly Ala Ile Thr Arg Gly Ala Thr Val Thr
            520                 525                 530

CGA GGC GTG CCA CCC CCA CCT ACT GTG AGG GGT GCT CCA GCA CCA AGA    432
Arg Gly Val Pro Pro Pro Pro Thr Val Arg Gly Ala Pro Ala Pro Arg
    535                 540                 545

GCA CGG ACA GCG GGC ATC CAG AGG ATA CCT TTG CCT CCA CCT CCT GCA    480
Ala Arg Thr Ala Gly Ile Gln Arg Ile Pro Leu Pro Pro Pro Pro Ala
550                 555                 560                 565

CCA GAA ACA TAT GAA GAA TAT GGA TAT GAT GAT ACA TAC GCA GAA CAA    528
Pro Glu Thr Tyr Glu Glu Tyr Gly Tyr Asp Asp Thr Tyr Ala Glu Gln
                570                 575                 580

AGT TAC GAA GGC TAC GAA GGC TAT TAC AGC CAG AGT CAA GGG GAC TCA    576
Ser Tyr Glu Gly Tyr Glu Gly Tyr Tyr Ser Gln Ser Gln Gly Asp Ser
            585                 590                 595

GAA TAT TAT GAC TAT GGA CAT GGG GAG GTT CAA GAT TCT TAT GAA GCT    624
Glu Tyr Tyr Asp Tyr Gly His Gly Glu Val Gln Asp Ser Tyr Glu Ala
            600                 605                 610

TAT GGC CAG GAC GAC TGG AAT GGG ACC AGG CCG TCG CTG AAG GCC CCT    672
Tyr Gly Gln Asp Asp Trp Asn Gly Thr Arg Pro Ser Leu Lys Ala Pro
    615                 620                 625

CCT GCT AGG CCA GTG AAG GGA GCA TAC AGA GAG CAC CCA TAT GGA CGT    720
Pro Ala Arg Pro Val Lys Gly Ala Tyr Arg Glu His Pro Tyr Gly Arg
630                 635                 640                 645

TAT TAA                                                            726
Tyr *

(2) INFORMATION FOR SEQ ID NO:6:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:6:

Met Arg Asp Lys Ala Lys Glu Glu Leu Arg Lys Gly Gly Asp Pro
1               5                   10                  15

Lys Tyr Ala His Leu Asn Met Asp Leu His Val Phe Ile Glu Val Phe
                20                  25                  30

Gly Pro Pro Cys Glu Ala Tyr Ala Leu Met Ala His Ala Met Glu Glu
            35                  40                  45
```

```
Val Lys Lys Phe Leu Val Pro Asp Met Met Asp Ile Cys Gln Glu
    50                  55                  60

Gln Phe Leu Glu Leu Ser Tyr Leu Asn Gly Val Pro Glu Pro Ser Arg
65                  70                  75                  80

Gly Arg Gly Val Pro Val Arg Gly Arg Gly Ala Ala Pro Pro Pro
                85                  90                  95

Pro Val Pro Arg Gly Arg Gly Val Gly Pro Pro Arg Gly Ala Leu Val
            100                 105                 110

Arg Gly Thr Pro Val Arg Gly Ala Ile Thr Arg Gly Ala Thr Val Thr
            115                 120                 125

Arg Gly Val Pro Pro Pro Thr Val Arg Gly Ala Pro Ala Pro Arg
130                 135                 140

Ala Arg Thr Ala Gly Ile Gln Arg Ile Pro Leu Pro Pro Pro Pro Ala
145                 150                 155                 160

Pro Glu Thr Tyr Glu Glu Tyr Gly Tyr Asp Asp Thr Tyr Ala Glu Gln
                165                 170                 175

Ser Tyr Glu Gly Tyr Glu Gly Tyr Tyr Ser Gln Ser Gln Gly Asp Ser
            180                 185                 190

Glu Tyr Tyr Asp Tyr Gly His Gly Glu Val Gln Asp Ser Tyr Glu Ala
            195                 200                 205

Tyr Gly Gln Asp Asp Trp Asn Gly Thr Arg Pro Ser Leu Lys Ala Pro
    210                 215                 220

Pro Ala Arg Pro Val Lys Gly Ala Tyr Arg Glu His Pro Tyr Gly Arg
225                 230                 235                 240

Tyr
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:7:

CAGCTGCTGA CGGCAGAAAT TGAG                        24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:8:

TTAATAACGT CCATATGGGT GCTC                        24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "Oligonucleotide"

(xi) SEQUENCE DESCRIPTION: SEQ ID NO:9:

CAGTATCCCA AGGAGGAAGA GCTG                                              24

(2) INFORMATION FOR SEQ ID NO:10:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(xi) SEQUENCE DESCRIPTION: SEQ ID NO:10:

CTGTCAAGCA GTATCCCAAG GAGG                                              24

(2) INFORMATION FOR SEQ ID NO:11:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(xi) SEQUENCE DESCRIPTION: SEQ ID NO:11:

AAGGGCTCAA TGAGAGACAA AGCC                                              24

(2) INFORMATION FOR SEQ ID NO:12:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(xi) SEQUENCE DESCRIPTION: SEQ ID NO:12:

GTATGTATCA TCATATCCAT ATTC                                              24
```

ΔP62, VARIANTS THEREOF, AMINO ACID SEQUENCES CODING THEREFOR AND THEIR USES IN GENE THERAPY FOR CANCER

CROSS-REFERENCES TO RELATED APPLICATIONS

This application is a §371 national phase filing of International Application No. PCT/FR96/00802, filed May 29, 1996.

BACKGROUND OF THE INVENTION

1. Field of the Invention

The present invention relates to a new polypeptide designated ΔP62, to its variants, to the corresponding nucleic acid sequences and to their therapeutic uses, in particular in anticancer gene therapy.

2. Description of Related Art

Various genes, referred to as oncogenes and suppressor genes, are involved in the control of cell division. Among these, the ras genes and their products, generally designated p21 proteins, perform a key role in the control of cell proliferation in all the eukaryotic organisms in which they have been sought. In particular, it has been shown that certain specific modifications of these proteins cause them to lose their normal control and lead them to become oncogenic. Thus, a large number of human tumours have been associated with the presence of modified ras genes. Similarly, an overexpression of these p21 proteins can lead to a deregulation of cell proliferation. An understanding of the exact role of these p21 proteins in cells, their mode of functioning and their characteristics hence constitutes a most profitable focus of attention for our understanding of carcinogenesis and the therapeutic approach thereto.

In vivo, the precise nature of the events responsible for transduction of the signal initiated by the p21 proteins is not known. However, an increasing number of results highlight the multiplicity of effectors which interact directly and preferentially with the active form (bound to GTP) of the ras proteins. Among these effectors, the GAP protein has been the first one to have its involvement in the transduction of the signal documented. It is a cytosol protein, present in all eukaryotic organisms, which possesses the faculty of strongly accelerating the hydrolysis of the GTP bound to the normal protein. It possesses two domains providing for different functions. Its carboxy-terminal end carries the catalytic activity which interacts with the p21 proteins and which increases their GTPase activity. At its other end, downstream of the N-terminal portion, there is a juxtaposition of SH2 and SH3 domains which participate in the transduction of the message and interact with other proteins. Among these proteins, there are two, p62 and p190, of 62 kDa and 190 kDa, respectively, in which the tyrosine is strongly phosphorylated. These two proteins form a specific complex with GAP and are immunoprecipitated by antibodies directed against different epitopes of GAP. It is known, in particular, that the SH2 domains of GAP are the regions in which the interactions of p62 with GAP take place. Amino acids 271 to 443 of p62 contain phosphorylated tyrosines and appear to be involved in these interactions. These same phosphorylations appear, moreover, to participate in interactions between p62 and the adapter GRB2. Moreover, along the whole length of the p62 sequence, proline-rich consensus sites are distributed which participate in the binding to the SH3 domains of the tyrosine kinases of the src family, and also of phospholipase Cγ.

The p62 (or alternatively Sam68) protein was identified by Wong et al. (Cell 69 (1992) 551). It contains 443 amino acids, the sequence of which has been described in the literature (see SEQ ID No. 2).

In addition to the features mentioned above, the p62 protein displays several features characteristic of hnRNPs (heterogeneous nuclear ribonucleoproteins):

it is rich in glycines it possesses regions rich in arginines furthermore, its amino acids 145 to 247 define a region of strong homology with an hnRNP described previously, GRP33. This region contains a consensus binding site for RNAs which is homologous to the one contained in hnRNP K. This consensus site is designated KH domain (KH=hnRNPK Homologue). The conserved residues are essential to the binding to RNAs, and the impact of the non-integrity of this domain in a pathology has been shown for FMR1, which is the product of the gene associated with mental retardation which is observed in fragile X syndrome (Siomi et al., Cell 77 (1994) 33).

SUMMARY OF THE INVENTION

The present invention has its basis, in particular, in the demonstration of the importance of the p62 (Sam68) protein in cell proliferation and death. It is the outcome, more especially, of the demonstration that p62 derivatives are capable of interfering in the process of cell transformation, and in particular of inhibiting the signals transduced by the ras and arc proteins. It is the outcome, in addition, of the especially surprising demonstration that these derivatives are also endowed with apoptotic properties, and hence capable of inducing cell death.

A first subject of the invention hence relates to any p62 derivative capable of at least partially inhibiting the interaction between a GAP protein and p62. Preferably, the derivatives according to the invention are capable of at least partially inhibiting the oncogenic power of the ras and/or arc proteins. Still more preferably, the derivatives according to the invention are capable of inducing cell death by apoptosis. The derivatives according to the invention are also characterized by the loss of the capacity to interact with RNA of p62.

The present invention describes, in particular, the demonstration, cloning and characterization of a natural isoform of the p62 protein. This isoform, designated Δp62 (or ΔSam68), possesses a deletion in the zone of homology to the GRP33 protein, which covers the KH domain. As a result of this deletion, Δp62 does not possess the properties of p62 in their entirety. Thus, Δp62 possesses a domain of interaction with GAP and intact GRB2, as well as the various proline-rich sequences which are partners of SH3 (FIG. 1). However, Δp62 is no longer capable of interacting with nucleic acids as a result of the deletion of the domain of homology to the GRP33 protein. The Applicant also showed that the transfer of Δp62 cDNA in various normal or tumoral cell models impedes the cooperation between p62 and Ras and inhibits the signals transduced by normal and oncogenic Ras proteins. Hence, when overexpressed, Δp62 interferes with the processes of proliferation and differentiation and leads, in the different cell models, to cell death by apoptosis.

According to a preferred embodiment, the invention relates more especially to any p62 derivative carrying at least one deletion in the zone of homology to the GRP33 protein. More especially, the derivatives according to the invention contain at least one deletion in the region lying between residues 145 and 247 of the p62 protein as shown in the sequence SEQ ID No. 1, and which covers the KH domain. The deletion advantageously involves more than 10 amino acids, and more preferably involves more than 30 amino acids. It can affect one or several sites within this region, provided the resulting derivative displays the properties described above.

It is especially advantageous for the derivative according to the invention to be a polypeptide comprising all or part of the sequence SEQ ID No. 4 or of a variant of the latter. For the purposes of the invention, the term variant denotes any polypeptide whose structure differs from the sequence SEQ ID No. 4 by one or more modifications of a genetic, biochemical and/or chemical nature. Such modifications can entail, in particular, any mutation, substitution, deletion, addition and/or modification of one or more residues. Such derivatives may be generated for different purposes, such as, in particular, that of increasing the affinity of the peptide for its interaction site, that of improving its levels of production, that of increasing its resistance to proteases or of improving its passage through cell membranes, that of increasing its therapeutic efficacy or of reducing its side effects or that of endowing it with new pharmacokinetic and/or biological properties. Advantageously, the variants comprise deletions or mutations involving amino acids whose presence is not decisive for the activity of the derivative. Such amino acids may be identified, for example, by tests of cellular activity as described in the examples.

As a special preference, the derivatives of the invention retain at least a portion of the p62 protein permitting the interaction with the SH2 domain of GAP. This portion of p62 consists, more especially, of phosphorylated tyrosines localized between residues 200 and 443 of the p62 protein (see SEQ ID No. 2). A preferred derivative according to the invention hence comprises at least (i) a deletion in the region lying between residues 145 and 247 of p62, and (ii) a portion of p62 permitting the interaction with the SH2 domain of GAP. More preferably, the deletion involves residues 1 to 202.

In this connection, the Applicant also showed that derivatives according to the invention displaying especially advantageous properties can consist of polypeptides essentially comprising the region carrying the phosphorylated tyrosines of p62.

An especially preferred example of polypeptide according to the invention is represented by the polypeptide Δp62 of sequence SEQ ID No. 4, possessing a deletion of residues 170–208 of the sequence of p62. Another example is represented by the polypeptide p62-C comprising residues 203 to 443 of p62 (sequence SEQ ID No. 6).

The results presented in the present application show, in particular, that Δp62 can compete with p62 for GAP. Since GAP is one of the effectors of the Ras proteins, Δp62 blocks the mitogenic pathways dependent thereon. When overexpressed by gene transfer (transfection, infection, microinjection, and the like), Δp62 induces cell death by apoptosis in normal cells (NIH3T3 and Swiss 3T3 fibroblasts) or tumour cells (H460;HCT116), and is capable of inhibiting the formation of foci induced by ras. This same effect is obtained with the derivative p62-C (essentially comprising the C-terminal portion of Δp62, which covers the region lying between amino acids 203 and 443 and which corresponds to the domain of interaction with the SH2 domains of GAP and of GRB2). This C-terminal portion also contains three of the sites of interaction with the SH3 domains, those having most affinity for Fyn. The substantial therapeutic activity of the derivatives according to the invention is associated with their multifarious properties, and in particular their power of titration of the SH3 domains of proteins of the src family (for example fyn), their capacity for inhibition of the recruitment of GRB2 by titrating its SH2 domain and their capacity for inhibition of the effector function of the GAP protein for the Ras dependent pathways of signalling.

Another subject of the present invention relates to any nucleic acid coding for a polypeptide as defined above.

The nucleic acid according to the invention can be a ribonucleic acid (RNA) or a deoxyribonucleic acid (DNA). In addition, it can be a genomic DNA (gDNA) or complementary DNA (cDNA). It may be of human, animal, viral, synthetic or semi-synthetic origin. It may be obtained in various ways, and in particular by chemical synthesis using the sequences presented in the application and, for example, a nucleic acid synthesizer. It may also be obtained by the screening of libraries by means of specific probes, in particular such as the ones described in the application (see sequences SEQ ID No. 9 and 10, for example). It may also be obtained by mixed techniques including chemical modification (elongation, deletion, substitution, and the like) of sequences screened from libraries. Generally speaking, the nucleic acids of the invention may be prepared according to any technique known to a person skilled in the art.

Preferably, the nucleic acid according to the invention is a cDNA or an RNA.

The nucleic acid according to the invention is advantageously chosen from:

(a) all or part of the sequence SEQ ID No. 3 or SEQ ID No. 5 or of their complementary strand, (b) any sequence hybridizing with the sequences (a) and coding for a derivative according to the invention, (c) the variants of (a) and (b) resulting from the degeneracy of the genetic code.

As mentioned above, the Applicant has now isolated and characterized new nucleic acid sequences coding for polypeptides derived from p62, having altogether exceptional antiproliferative and apoptotic properties. These nucleic acids may now be used as therapeutic agents for producing in cells derivatives according to the invention capable of destroying or correcting cellular dysfunctions. To this end, the present invention also relates to any expression cassette comprising a nucleic acid as defined above, a promoter permitting its expression and a transcription termination signal. The promoter is advantageously chosen from promoters which are functional in mammalian, preferably human, cells. More preferably, it is a promoter permitting the expression of a nucleic acid in a hyperproliferative cell (cancer cell, restenosis, and the like). In this connection, various promoters may be used. For example, the p62 gene's own promoter may be used. Promoter regions of different origin (responsible for the expression of other proteins, or even synthetic regions) may also be used. Thus, it is possible to use any promoter or derived sequence that stimulates or represses the transcription of a gene, specifically or otherwise, inducibly or otherwise, strongly or weakly. The promoter sequences of eukaryotic or viral genes may be mentioned in particular. For example, the promoter sequences may be ones originating from the genome of the target cell. Among the eukaryotic promoters, it is possible to use, in particular, ubiquitous promoters (promoter of the HPRT, PGK, α-actin, tubulin, and the like, genes), promoters of intermediate filaments (promoter of the GFAP, desmin, vimentin, neurofilaments, keratin, and the like, genes), promoters of therapeutic genes (for example the promoter of the MDR, CFTR, factor VIII, ApoAI, and the like, genes), tissue-specific promoters (promoter of the pyruvate kinase, villin, intestinal fatty acid binding protein, smooth muscle α-actin, or the like, gene) or alternatively promoters that respond to a stimulus (steroid hormone receptor, retinoic acid receptor, and the like). Similarly, promoter sequences originating from the genome of a virus may be used, such as, for example, the promoters of the adenovirus E1A and MLP genes, the CMV early promoter or alternatively the RSV LTR promoter, and the like. In addition, these promoter regions may be modified by adding activating or regulatory sequences, or sequences permitting a tissue-specific or -preponderant expression.

The present invention now provides new therapeutic agents which make it possible, as a result of their antiproliferative and/or apoptotic properties, to interfere with a large number of cellular dysfunctions. For this purpose, the nucleic acids or cassettes according to the invention may be injected as they are at the site to be treated, or incubated directly with the cells to be destroyed or treated. It has, in effect, been reported that naked nucleic acids can enter cells without a special vector. Nevertheless, it is preferable in the context of the present invention to use an administration vector, enabling (i) the efficacy of cell penetration, (ii) targeting and (iii) extra- and intracellular stability to be improved.

According to an especially preferred embodiment of the present invention, the nucleic acid or cassette is incorporated in a vector. The vector used may be of chemical origin (liposome, nanoparticle, peptide complex, cationic polymers or lipids, and the like) viral origin (retrovirus, adenovirus, herpesvirus, AAV, vaccinia virus, and the like) or plasmid origin.

The use of viral vectors is based on the natural transfection properties of viruses. It is thus possible to use, for example, adenoviruses, herpesviruses, retroviruses and adeno-associated viruses. These vectors prove especially efficacious is from the standpoint of transfection. In this connection, a preferred subject according to the invention lies in a defective recombinant retrovirus whose genome comprises a nucleic acid as defined above. Another particular subject of the invention lies in a defective recombinant adenovirus whose genome comprises a nucleic acid as defined above.

The vector according to the invention can also be a non-viral agent capable of promoting the transfer of nucleic acids into eukaryotic cells and their expression therein. Synthetic or natural chemical or biochemical vectors represent an advantageous alternative to natural viruses, especially on grounds of convenience and safety and also on account of the absence of theoretical limit regarding the size of the DNA to be transfected. These synthetic vectors have two main functions, to compact the nucleic acid to be transfected and to promote its binding to the cell as well as its passage through the plasma membrane and, where appropriate, the two nuclear membranes. To mitigate the polyanionic nature of nucleic acids, the non-viral vectors all possess polycationic charges.

The nucleic acid or vector used in the present invention may be formulated for the purpose of administration topically, orally, parenterally, intranasally, intravenously, intramuscularly, subcutaneously, intraocularly, transdermally and the like. Preferably, the nucleic acid or vector is used in an injectable form. It may hence be mixed with any pharmaceutically acceptable vehicle for an injectable formulation, in particular for a direct injection at the site to be treated. The formulation may comprise, in particular, isotonic sterile solutions, or dry, in particular lyophilized, compositions which, on addition of sterilized water or of physiological saline as appropriate, enable injectable solutions to be made up. A direct injection of the nucleic acid into the patient's tumour is advantageous, since it enables the therapeutic effect to be concentrated in the tissues affected. The doses of nucleic acid used may be adapted in accordance with various parameters, and in particular in accordance with the gene, the vector, the mode of administration used, the pathology in question or alternatively the desired length of treatment.

The invention also relates to any pharmaceutical composition comprising at least one nucleic acid.

It also relates to any pharmaceutical composition comprising at least one vector as defined above.

It also relates to any pharmaceutical composition comprising at least one p62 derivative as defined above.

As a result of their antiproliferative properties, the pharmaceutical compositions according to the invention are most especially well suited to the treatment of hyperproliferative disorders such as, in particular, cancers and restenosis. Thus the present invention provides an especially effective method for the destruction of cells, in particular hyperproliferative cells. It may be used in vitro or ex vivo. Ex vivo, it consists essentially in incubating the cells in the presence of one or more nucleic acids (or of a vector or cassette or of the derivative directly). In vivo, it consists in administering to the body an active amount of a vector (or cassette) according to the invention, preferably directly at the site to be treated (tumour in particular). In this connection, the subject of the invention is also a method of destruction of hyperproliferative cells, comprising the bringing of the said cells or of a portion of them into contact with a nucleic acid as defined above.

The present invention is advantageously used in vivo for the destruction of hyperproliferating (i.e. abnormally proliferating) cells. It is thus applicable to the destruction of tumour cells or smooth muscle cells of the vascular wall (restenosis). It is most especially suitable for the treatment of cancers in which an activated oncbgene is involved. As an example, there may be mentioned adenocarcinoma of the colon, thyroid cancer, carcinoma of the lung, myeloid leukaemia, colorectal cancer, breast cancer, lung cancer, stomach cancer, cancer of the oesophagus, B lymphoma, ovarian cancer, bladder cancer, glioblastoma, hepatocarcinoma, cancer of the bone, skin and pancreas or alternatively kidney and prostate cancer, and the like.

The products of the invention are also useful for the identification of other partners of the pathways of signalling of oncogenes, by testing for inhibitors, agonists, competitors or molecules that interact in vivo with these products.

Moreover, the invention also relates to antisense sequences whose expression a target cell enables the transcription and/or translation of cellular mRNAs coding for p62 or Δp62 to be controlled. Such sequences can, for example, be transcribed in the target cell into RNAs complementary to the Δp62 or p62 cellular mRNAs, and can thus block their translation into protein, according to the technique described in Patent EP 140,308. Such sequences can consist of all or part of the nucleic acid sequences SEQ ID NO. 1, 3 or 5, transcribed in the reverse orientation.

The present invention also relates to the use of any compound capable of inducing the expression or overexpression of Δp62 in a cell, for the preparation of a pharmaceutical composition intended for the treatment of hyperproliferative disorders.

The present invention will be described in greater detail by means of the examples which follow, which are to be considered to be illustrative and non-limiting.

BRIEF DESCRIPTION OF THE DRAWINGS

Legends to the Figures

DETAILED DESCRIPTION OF THE INVENTION

General Techniques of Molecular Biology

Figure 1:
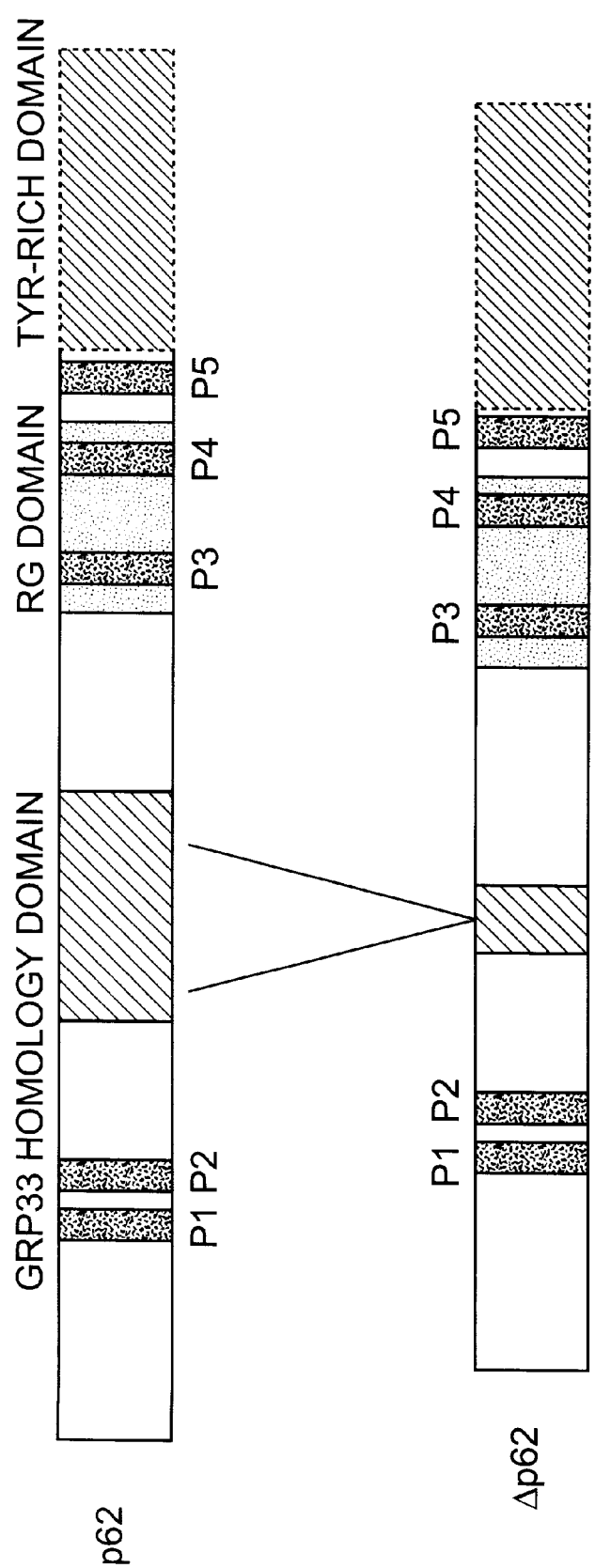
FIG. 1: Diagrammatic representation of the structural domains of p62 and Δp62.

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol-chloroform extraction of proteins, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories). To carry out ligation, the DNA fragments may be separated according to their size by agarose or acrylamide gel electrophoresis, extracted with phenol or with a phenol-chloroform mixture, precipitated with ethanol and then incubated in the presence of phage T4 DNA ligase (Biolabs) according to the supplier's recommendations. The filling in of 5' protruding ends; may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

In vitro site-directed mutagenesis using synthetic oligodeoxynucleotides may be performed according to the method developed by Taylor et al. [Nucleic Acids Res. 13 (1985) 8749–8764] using the kit distributed by Amersham. The enzymatic amplification of DNA fragments by the so-called PCR [polymerase-catalysed chain reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications. Verification of the nucleotide sequences may be performed by the method developed by Sanger et al. [Proc. Natl. Acad. Sci. USA, 74 (1977) 5463–5467] using the kit distributed by Amersham.

EXAMPLES

Example 1

Isolation of Δp62 Complementary DNA

Δp62 complementary DNA was isolated by PCR on a population of complementary DNA Synthesized from poly (A)+RNAs extracted from human placenta. 1 μg of DNA was used jointly with primers derived from the sequence of p62 and which cover amino acids 123 to 131 on the one hand (5' oligo) and 437 to 443 on the other hand (3' oligo). The sequences of these primers are as follows:

5' oligo: CAGCTGCTGACGGCAGAAATTGAG (SEQ ID No. 7)

3' oligo: TTMTMCGTCCATATGGGTGCTC (SEQ ID No. 8)

The reactions were carried out at 55° C. and gave two products separated by agarose gel electrophoresis:

a band of 987 base pairs which corresponds to the PCR product of p62 a band of 870 base pairs which corresponds to the PCR product of Δp62.

The latter band was cloned, and its sequence corresponds exactly to the sequence of p62 except for a deletion of 117 base pairs in the domain of homology to GRP33. The complete sequence of Δp62 is presented as SEQ ID No. 3 (see also FIG. 1).

The existence of this isoform of p62 was confirmed by screening a library of human placental complementary DNA, established in the vector λgt 11. The oligonucleotide used for this screening is a 24-mer corresponding to the specific junction of the deletion present in Δp62. The sequence of this oligonucleotide is:

CAGTATCCCMGGAGGMGAGCTG (SEQ ID No. 9)

Example 2

Construction of Vectors for the Expression of Δp62 and p62-C

This example describes the construction of vectors which can be used for transfer of the nucleic acids of the invention in vitro or in vivo.

2.1. Plasmid vector:

For the construction of plasmid vectors, two types of vector were used.

The vector SV2, described in DNA Cloning, A practical approach Vol. 2, D. M. Glover (Ed) IRL Press, Oxford, Washington D.C., 1985. This vector is a eukaryotic expression vector. The nucleic acids coding for the variants p62-C and Δp62 were inserted into this vector in the form of EcoRI fragments. They are thus placed under the control of the promoter of the SV40 virus enhancer.

The vector pcDNA3 (Invitrogen). This is also a eukaryotic expression vector. The nucleic acids coding for the variants p62-C and Δp62 were inserted into this vector in the form of EcoRI fragments, and are thus placed under the control of the CMV early promoter.

2.2. Viral vector

According to a particular embodiment, the invention lies in the construction and use of viral vectors permitting the transfer and expression in vivo of the nucleic acids as defined above.

As regards adenoviruses more especially, various serotypes whose structure and properties vary somewhat have been characterized. Among these serotypes, it is preferable to use, in the context of the present invention, human adenoviruses type 2 or 5 (Ad 2 or Ad 5) or adenoviruses of animal origin (see Application WO94/26914). Among adenoviruses of animal origin which can be used in the context of the present invention, adenoviruses of canine, bovine, murine (for example Mavl, Beard et al., Virology 75 (1990) 81), ovine, porcine, avian or alternatively simian (for example SAV) origin may be mentioned. Preferably, the adenovirus of animal origin is a canine adenovirus, and more preferably a CAV2 adenovirus [strain Manhattan or A26/61 (ATCC VR-800) for example]. Preferably, adenoviruses of human or canine or mixed origin are used in the context of the invention.

Preferably, the defective adenoviruses of the invention comprise the ITRs, a sequence permitting encapsidation and a nucleic acid according to the invention. Still more preferably, in the genome of the adenoviruses of the invention, the E1 region at least is non-functional. The viral gene in question may be rendered non-functional by any technique known to a person skilled in the art, and in particular by total elimination, substitution, partial deletion or addition of one or more bases in the gene or genes in question. Such modifications may be obtained in vitro (on the isolated DNA) or in situ, for example by means of genetic engineering techniques, or alternatively by treatment by means of mutagenic agents. Other regions may also be modified, and in particular the E3 region (WO95/02697), E2 region (WO94/28938), E4 region (WO94/28152, WO94/12649, WO95/02697) and L5 region (WO95/02697). According to a preferred embodiment, the adenovirus according to the invention comprises a deletion in the E1 and E4 regions. According to another preferred embodiment, it comprises a deletion in the E1 region into which are inserted the E4 region and the nucleic acid of the invention (see FR94/13355). In the viruses of the invention, the deletion in the E1 region preferably extends from nucleotides 455 to 3329 on the sequence of the Ad5 adenovirus.

The defective recombinant adenoviruses according to the invention may be prepared by any technique known to a person skilled in the art (Levrero et al., Gene 101 (1991) 195, EP 185,573; Graham, EMBO J. 3 (1984) 2917). In particular, they may be prepared by homologous recombination between an adenovirus and a plasmid carrying, inter alia, the DNA sequence of interest. Homologous recombination takes place after cotransfection of the said adenovirus and said plasmid into a suitable cell line. The cell line used should preferably (i) be amenable to transformation by the said elements, and (ii) contain the sequences capable of complementing the portion of the genome of the defective adenovirus, preferably in integrated form in order to avoid the risks of recombination. As an example of a line, there may be mentioned the human embryonic kidney line 293 (Graham et al., J. Gen. Virol. 36 (1977) 59), which contains, in particular, integrated in its genome, the left-hand portion of the genome of an Ad5 adenovirus (12%), or lines capable of complementing the E1 and E4 functions, as described, in particular, in Applications Nos. WO94/26914 and WO95/02697.

Thereafter, the adenoviruses which have multiplied are recovered and purified according to standard techniques of molecular biology, as illustrated in the examples.

Regarding adeno-associated viruses (AAV), the latter are relatively small DNA viruses which integrate stably and site-specifically in the genome of the cells they infect. They are capable of infecting a broad spectrum of cells without inducing an effect on growth, morphology or cell differentiation. Moreover, they do not appear to be involved in pathologies in man. The AAV genome has been cloned, sequenced and characterized. It comprises approximately 4700 bases, and contains at each end an inverted repeat region (ITR) of approximately 145 bases serving as origin of replication for the virus. The remainder of the genome is divided into 2 essential regions carrying the encapsidation functions: the left-hand portion of the genome, which contains the rep gene involved in viral replication and expression of the viral genes; and the right-hand portion of the genome, which contains the cap gene coding for the capsid proteins of the virus.

The use of vectors derived from AAV for gene transfer in vitro and in vivo has been described in the literature (see, in particular, WO91/18088; WO93/09239; U.S. Pat. Nos. 4,797,368, 5,139,941, EP 488,528). These applications describe various constructions derived from AAV, in which the rep and/or cap genes are deleted and replaced by a gene of interest, and their use for transferring the said gene of interest in vitro (on cells in culture) or in vivo (directly into a body). The defective recombinant AAVs according to the invention may be prepared by cotransfection, into a cell line infected with a human helper virus (for example an adenovirus), of a plasmid containing a nucleic acid sequence of the invention of interest flanked by two AAV inverted repeat regions (ITR) and of a plasmid carrying the AAV encapsidation genes (rep and cap genes). A cell line which can be used is, for example, the 293 line. The recombinant AAVs produced are then purified by standard techniques.

Regarding herpesviruses and retroviruses, the construction of recombinant vectors has been amply described in the literature: see, in particular, Breakfield et al., New Biologist 3 (1991) 203; EP 453,242, EP 178,220, Bernstein et al., Genet, Eng. 7 (1985) 235; McCormick, BioTechnology 3 (1985) 689, and the like. In particular, retroviruses are integrative viruses that selectively infect dividing cells. Hence they constitute vectors of interest for cancer applications. The genome of retroviruses essentially comprises two LTRs, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be prepared from different types of retrovirus such as, in particular, MoMuLV (Murine moloney leukaemia virus, also designated MoMLV), MSV (Murine moloney sarcoma virus), HaSV (Harvey sarcoma virus), SNV (spleen necrosis virus), RSV (Rous sarcoma virus) or alternatively Friend virus.

To construct recombinant retroviruses according to the invention containing a nucleic acid according to the invention, a plasmid containing, in particular, the LTRs, the encapsidation sequence and the said nucleic acid is constructed, and is then used to transfect a so-called encapsidation cell line capable of supplying in trans the retroviral functions which are deficient in the plasmid. Generally, the encapsidation lines are hence capable of expressing the gag, pol and env genes. Such encapsidation lines have been described in the prior art, and in particular the PA317 line (U.S. Pat. No. 4,861,719), the PsiCRIP line (WO90/02806) and the GP+envAm-12 line (WO89/07150). Moreover, the recombinant retroviruses can contain modifications in the LTRs in order to abolish transcriptional activity, as well as extended encapsidation sequences containing a portion of the gag gene (Bender et al., J. Virol. 61 (1987) 1639). The recombinant retroviruses produced are then purified by standard techniques.

To carry out the present invention, it is most especially advantageous to use a defective recombinant adenovirus or retrovirus. These vectors possess, in effect, especially advantageous properties for the transfer of genes into tumour cells.

2.3. Chemical vector

Among the synthetic vectors developed, it is preferable to use, in the context of the invention, cationic polymers of polylysine, $(LKLK)_n$, $(LKKL)_n$, polyethylenimine and DEAE-dextran type, or alternatively cationic lipids or lipofectants. They possess the property of condensing DNA and of promoting its association with the cell membrane. Among these latter vectors, lipopolyamines (lipofectamine, transfectam, and the like) and various cationic or neutral lipids (DOTMA, DOGS, DOPE, and the like), as well as peptides of nuclear origin, may be mentioned. In addition, the concept of receptor-mediated targeted transfection has been developed, which turns to good account the principle of condensing DNA by means of the cationic polymer while directing the binding of the complex to the membrane by means of a chemical coupling between the cationic polymer and the ligand for a membrane receptor, present at the surface of the cell type. which it is desired to graft. The targeting of the transferrin or insulin receptor or of the asialoglycoprotein receptor of hepatocytes has thus been described. The preparation of a composition according to the invention using a chemical vector of this kind is carried out according to any technique known to a person skilled in the art, generally by simply bringing the different components into contact.

Example 3

Figure 2:
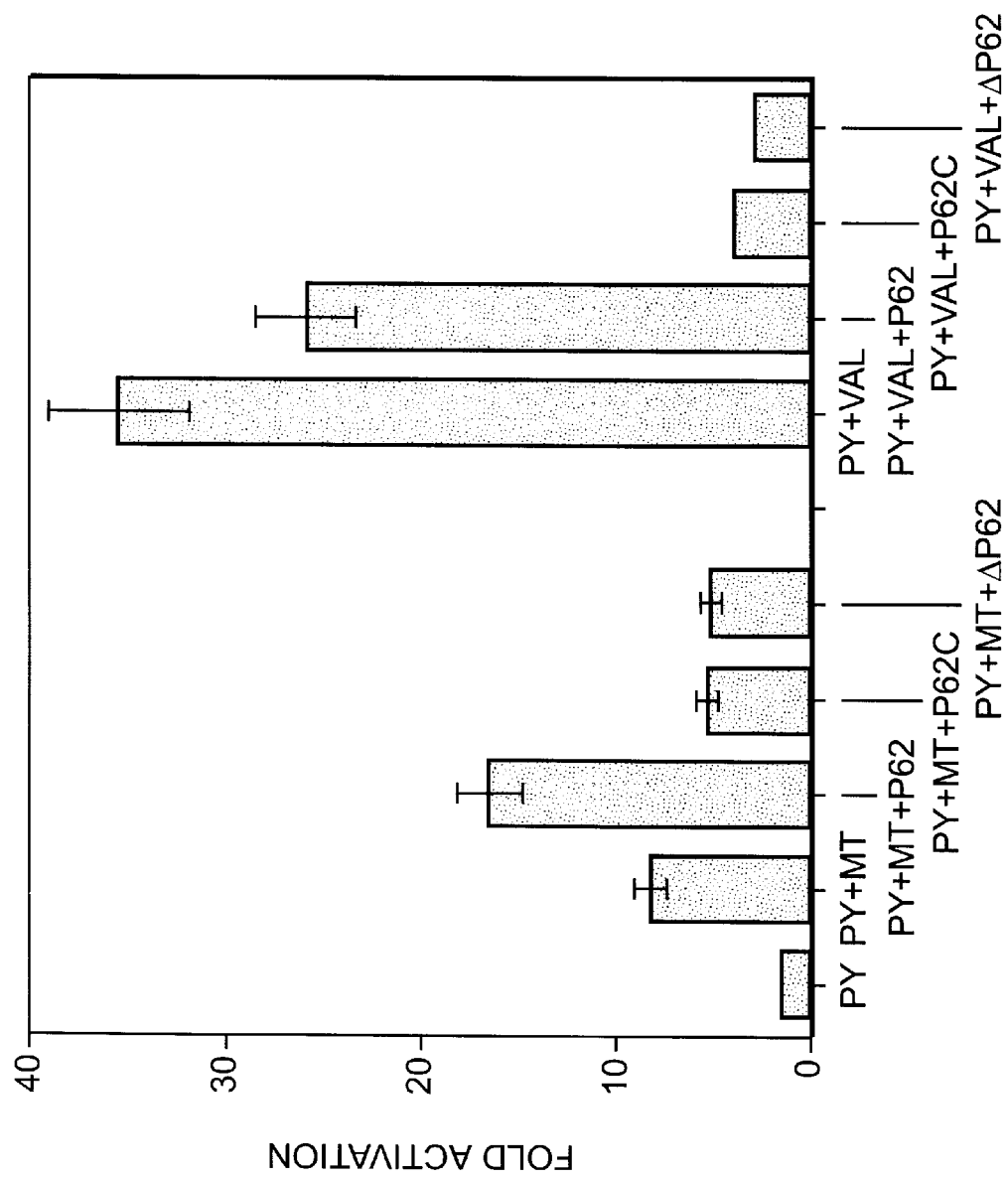
FIG. 2: Effect of p62 and Δp62 on the transactivation by ras proteins of an RRE derived from the enhancer of polyoma virus.

Inhibition of the Transactivation of RRE (Ras Responsive Elements) Due to the Oncogenic Forms of Ras (FIG. 2)

NIH 3T3 fibroblasts were transfected with a reporter gene, that for chloramphenicol acetyltransferase, placed under the control of Ras responsive elements derived from the enhancer of polyoma virus. These elements are stimulated from 15- to 20-fold when the cells are cotransfected with an expression vector carrying the cDNA of the SV40 oncogene Middle T(MT). This stimulation is only slightly affected when a cotransfection supplies the vectors for the expression of p62-C and of Δp62 (see Example 2). When the cotransfection is carried out with the activated form of the oncogene Ha-ras (Val 12) instead of with MT, the CAT activity is stimulated from 30- to 40-fold above the baseline level. The expression of p62 has little effect on this stimulation, whereas p62-C and Δp62 inhibit almost completely all activity due to the oncogenic Ras. In the same way, the stimulation obtained by cotransfection with the oncogene v-src is strongly inhibited by the p62-C and Δp62 proteins, but not by p62.

These experiments were carried out with 0.5 μg of vector permitting the expression of MT or of Ras VAL 12 or of v-src, and 4 μg of expression vector carrying the p62-C or Δp62 cDNA. They demonstrate clearly the power of the proteins of the invention to interfere with the oncogenic ras signals.

Example 4

Figure 3:
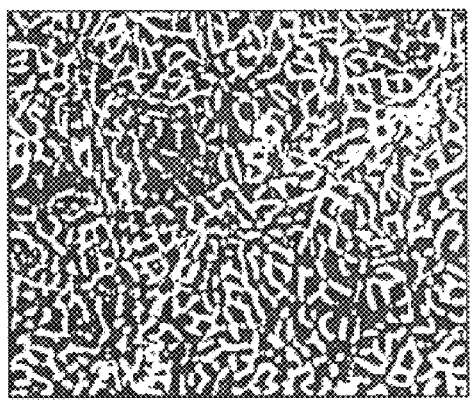
FIG. 3: Demonstration of Δp62-induced cell death in NIH3T3 fibroblasts.
Figure 3:
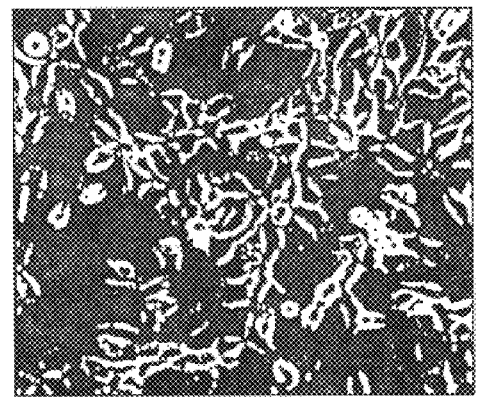

Demonstration of Δp62-induced Cell Death in NIH3T3 Fibroblasts (FIG. 3)

NIH3T3 fibroblasts were transfected with an efficiency of 60% with 5 μg of vector for the expression of Δp62 (Example 2).

24 hours after transfection, the cells display a considerable impairment of their viability with respect to the control. Analysis of their DNA reveals, after migration on agarose gel, scales of degradation characteristic of the phenomena of apoptosis. The same phenomena are observed when p62-C is transfected under the same conditions as Δp62.

Example 5

Figure 4:
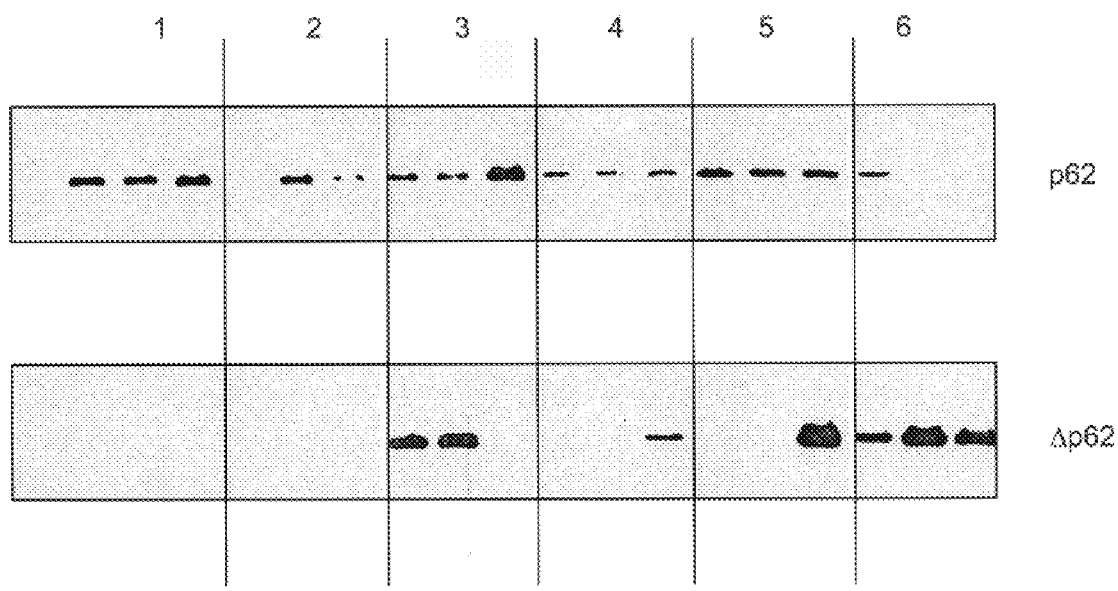
FIG. 4: Demonstration of the expression of Δp62 in embryonic fibroblasts treated with various cytotoxic agents and by deprivation of serum.

Demonstration of the Expression of Δp62 in Embryonic Fibroblasts Treated with Various Cytotoxic Agents and by Deprivation of Serum (FIG. 4)

Mouse embryonic fibroblasts were cultured (1), treated with 0.5 μg of okadaic acid (2), treated with 10 ng/ml of PMA and with 2 μg of ionomycin (3), subjected to 1 μM staurosporine (4) or to 2 μg/ml of camptothecin (5) and lastly deprived of serum.

The expression of the p62 and Δp62 messenger RNAs in these fibroblasts and during these various treatments was analysed. At each treatment, three points were analysed. These points correspond to three treatment times: 6, 12 and 24 hours.

5' probe specific for Δp62 (SEQ ID No. 10): CTGTCMG-CAGTATCCCAAGGAGG

5' probe specific for p62 (SEQ ID No. 11): AAGGGCT-CAATGAGAGACAAAGCC

3' probe common to p62 and to Δp62 (SEQ ID No. 12): GTATGTATCATCATATCCATATTC

In the fibroblasts cultured in the presence of 10% foetal calf serum (FCS), p62 mRNA is revealed, whereas Δp62 mRNA is not detected even after 24 hours of culturing. The situation is the same during treatment with okadaic acid. In contrast, a strong induction of Δp62 mRNA is observed after 6 to 12 hours of treatment with PMA and ionomycin. This mRNA is also detectable after the addition of staurosporine, and is very strongly induced after 12 hours of treatment with camptothecin. When the embryonic fibroblasts are deprived of serum, a strong induction of Δp62 is observed at the same time as a disappearance of the p62 messenger.

Hence these results demonstrate that the expression of Δp62 mRNA is induced in the course of certain apoptotic situations in fibroblasts.

Example 6

Inhibition by Δp62 of Ras-induced Foci Formation

This example describes another study showing that Δp62 interferes with the oncogene-induced transformation process. More especially, this example demonstrates that Δp62 is capable of inhibiting the formation of foci induced by various oncogenes (oncogenic ras, v-src) in NIH-3T3 cells, whereas p62 does not affect this phenomenon.

NIH3T3 fibroblasts were cotransfected with 0.1 μg of vector for the expression of v-Src or Ha-Ras Val12 and with 4 mg of vector for the expression of p62 or of Δp62 or empty vector (Example 2). The cells were maintained in medium containing 10% of newborn calf serum, and the number of foci was determined after fixation and staining of the cells in the presence of phenol-fuchsin. The experiments were carried out in triplicate.

Figure 5:
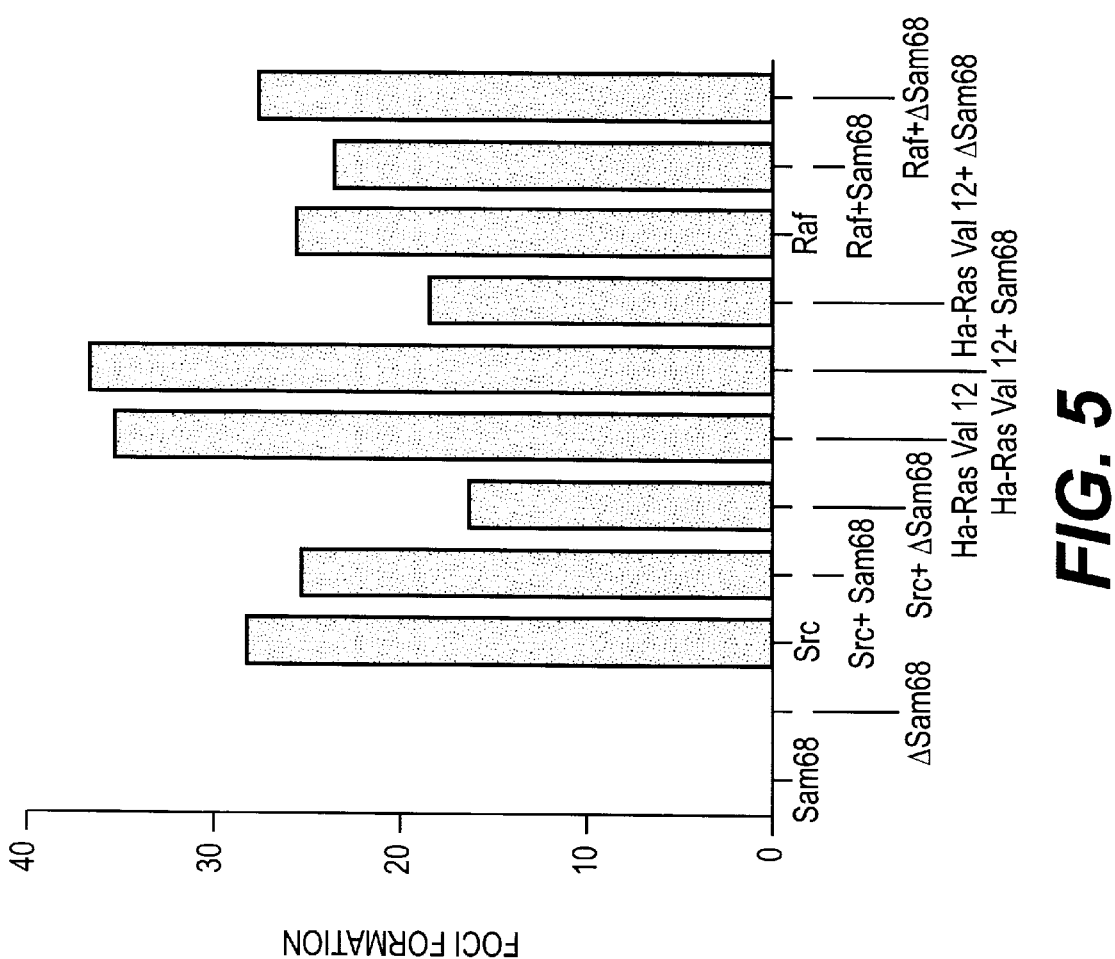
FIG. 5: Inhibition of oncogene-induced foci formation.

The results obtained are presented in FIG. 5. They show that Δp62 decreases the number of foci induced by v-src and Ha-Ras Val12 by approximately 50%. This effect reflects a specific antagonist power with respect to transformation by v-src and oncogenic Ha-Ras, since Δp62 does not affect the formation of foci induced by v-Raf. In addition, the observed effect is not associated with a toxicity of the product, since the number of neomycin-resistant colonies after transfection with p62, Δp62 or an empty vector is comparable. Hence these results confirm the inhibitory role of the molecules of the invention in the oncogene-induced transformation process. These results thus confirm the usefulness of these products in approaches of correction of the processes of cell proliferation induced by oncogenes, and also as a tool for the identification of other active molecules and/or those involved in the pathways of signalling of these oncogenes.

Example 7

Demonstration of an Interaction with Src in vivo

This example describes a study of the interaction of Δp62 with other molecules. It demonstrates that p62 and Δp62 are capable of interacting in vivo with src.

NIH3T3 fibroblasts were transfected with a vector for the expression of p62 or of Δp62 comprising an myc marker ("myc teg") (Example 2). The transfected cells were maintained In asynchronous growth or blocked in the mitotic phase by treatment with nocodazole. The cells were then cotransfected with a vector for the expression of v-Src or an empty vector. 48 hours later, the cells were lysed, and the complexes formed were immunodetected by means of anti-myc antibodies (9E10 antibodies) and anti-Src antibodies (N16 antibodies).

The results obtained show that p62 and Δp62 are capable of interacting in vivo with src. In addition, whereas the interaction between p62 and src appears to take place only in mitotic cells, Δp62 binds significantly to Src even in asynchronous cells. This interaction is strengthened in mitotic cells.

What is claimed is:

1. An isolated p62 derivative, wherein said derivative contains at least one deletion of at least one amino acid between amino acids 145–247 p62 (SEQ ID No. 2) and inhibits signals transduced by ras.

2. The p62 derivative according to claim 1, wherein said at least one deletion between amino acids 145–247 of p62 (SEQ ID No. 2) comprises a deletion of more than 10 amino acids.

3. An isolated p62 derivative according to claim 1, wherein the tyrosine residues are phosphorylated.

4. A pharmaceutical composition comprising a p62 derivative according to claim 1.

5. A composition comprising a p62 derivative according to claim 1.

6. An isolated polypeptide Δp62 comprising SEQ ID No. 4.

* * * * *

UNITED STATES PATENT AND TRADEMARK OFFICE
CERTIFICATE OF CORRECTION

PATENT NO. : 6,544,948 B1
DATED : April 8, 2003
INVENTOR(S) : Fabien Schweighoffer et al.

It is certified that error appears in the above-identified patent and that said Letters Patent is hereby corrected as shown below:

Column 29,
Line 53, "145-247 p62" should read -- 145-247 of p62 --.

Signed and Sealed this

Twelfth Day of August, 2003

JAMES E. ROGAN
*Director of the United States Patent and Trademark Office*